United States Patent [19]

Sommers et al.

[11] Patent Number: 5,140,996
[45] Date of Patent: Aug. 25, 1992

[54] CENTRAL VENOUS CATHETER PATIENT COVER

[75] Inventors: Jay R. Sommers, Marietta; Scott W. Dahl, Atlanta; Barry A. Michael, Roswell, all of Ga.

[73] Assignee: Kimberly-Clark Corporation, Neenah, Wis.

[21] Appl. No.: 811,100

[22] Filed: Dec. 20, 1991

[51] Int. Cl.⁵ .................... A61B 19/00; A61B 19/08
[52] U.S. Cl. ..................................... 128/849; 128/853
[58] Field of Search .................................. 128/849–856

[56] References Cited

U.S. PATENT DOCUMENTS

| | | | |
|---|---|---|---|
| 3,750,664 | 8/1973 | Collins | 128/853 |
| 3,881,474 | 5/1975 | Krzewinski | 128/852 |
| 3,956,048 | 5/1976 | Nord | 128/853 |
| 4,041,942 | 8/1977 | Dougan | 128/853 |
| 4,134,398 | 1/1979 | Scrivens | 128/852 |
| 4,489,720 | 12/1984 | Morris | 128/853 |
| 4,569,341 | 2/1986 | Morris | 128/853 |
| 4,596,245 | 6/1986 | Morris | 128/852 |
| 4,616,642 | 10/1986 | Martin | 128/853 |
| 4,869,271 | 9/1989 | Idris | 128/849 |

OTHER PUBLICATIONS

Kimberly-Clark Femoral Angiography Sheet With Window Code 79462.
Kimberly-Clark Femoral Angiography Sheet Code 79464.
Kimberly-Clark Femoral Angiography Drape Code 79700.

*Primary Examiner*—Michael Brown
*Attorney, Agent, or Firm*—Patrick C. Wilson

[57] ABSTRACT

Disclosed herein is a surgical drape or patient cover for use in central venous catheterizations of patients who require intravenous drug therapy and/or parenteral nutrition. The patient cover includes a mainsheet and a reinforcement sheet with two spaced apart triangular shaped fenestrations for use in the insertion of a central venous catheter into either the subclavian or basilic areas of the body.

3 Claims, 2 Drawing Sheets

CENTRAL VENOUS CATHETER PATIENT COVER

BACKGROUND OF THE INVENTION

The present invention relates to a surgical drape or patient cover. More specifically the present invention is directed to a surgical drape or patient cover for use in central venous catheterizations.

During the past decade, central venous catheters (CVCs) have become an important device for the successful management of cancer patients and others who require intravenous drug therapy and/or parenteral nutrition. Several complications prevent the prolonged maintenance of CVCs such as catheter site infection, suppurative phlebitis and septicemia. It has been reported that catheter-related septicemia represents the most frequent life-threatening complication with respect to central venous catheterization. There have been several reports (clinical and microbiological) that suggest that most vascular catheter-related septicemias are caused by microorganisms that invade the catheter-cutaneous tract during catheter insertion or while the catheter is in place. Therefore, adherence to aseptic techniques at the time of catheter insertion is important in attempting to minimize catheter-related infections. If the catheter becomes contaminated during insertion, a heavy microbial colonization and ultimately infection can result.

The current standard precautions for central venous catheter insertion require the inserter to wear sterile gloves and use a small (sterile or non-sterile, repellent or absorbent) drape or to square off the insertion area in triangular fashion with towels and clamps. Catheter-related infections as high as 18%-21% have been reported with such procedures. Performing this procedure with the current invention reduces this risk of infection.

In view of the relatively high risk of infection in connection with central venous catheterizations, there is therefore a need for a surgical drape or patient cover which will help reduce the risk of such infections. It is therefore an object of the present invention to provide a surgical drape or patient cover which can be used in connection with the catheterization of the veins in the subclavian and basilic areas. It is a further object of the present invention to provide such a surgical drape or patient cover which will allow access to the veins in the subclavian and basilic areas on either the left or the right hand side of the patient. These and other objects of the present invention will be become more apparent upon a further review of the specification, drawings and claims.

SUMMARY OF THE INVENTION

The present invention is directed to a surgical drape or patient cover for use in central venous catheterizations in the subclavian and basilic areas for intravenous drug therapy and/or parenteral nutrition.

The patient cover includes a mainsheet having a top surface and a bottom surface with a top edge and a bottom edge joined by opposed side edges. A reinforcement sheet is attached to the top surface of the mainsheet and is spaced equidistant from both of the opposed side edges of the mainsheet while being positioned between the top and bottom edges of the mainsheet such that the reinforcement sheet is closer to the top edge than to the bottom edge of the mainsheet. Both the mainsheet and reinforcement sheet in combination define a first fenestration and a second fenestration extending completely through both layers. Each of the fenestrations are triangular in shape with three apices and three sides. The triangular fenestrations are positioned in the patient cover such that one side of each triangle of each fenestration is parallel with one side of the other triangle. In addition, the two triangular fenestrations form a strip therebetween with generally parallel sides from the material of the mainsheet and reinforcements sheet which is approximately 1 to 6 inches in width. Furthermore, the fenestrations are positioned closer to the top edge than to the bottom edge of the mainsheet.

In a more specific embodiment of the present invention, one apex of each fenestration is closer to an adjacent one of the opposed side edges of the mainsheet than any other apices of the same fenestration and the fenestrations are symmetrically positioned about a longitudinal axis of the patient cover. If desired, each of the fenstrations can be covered with an incise material containing a port to expose a portion of a patient's skin for selective insertion of a central venous catheter in either the right or left hand side of the patient. This incise material is typically covered with an adhesive on its underside which is in turn covered by a release sheet which can be removed prior to the placement of the patient cover on the patient.

DESCRIPTION OF THE INVENTION

Figure 1:
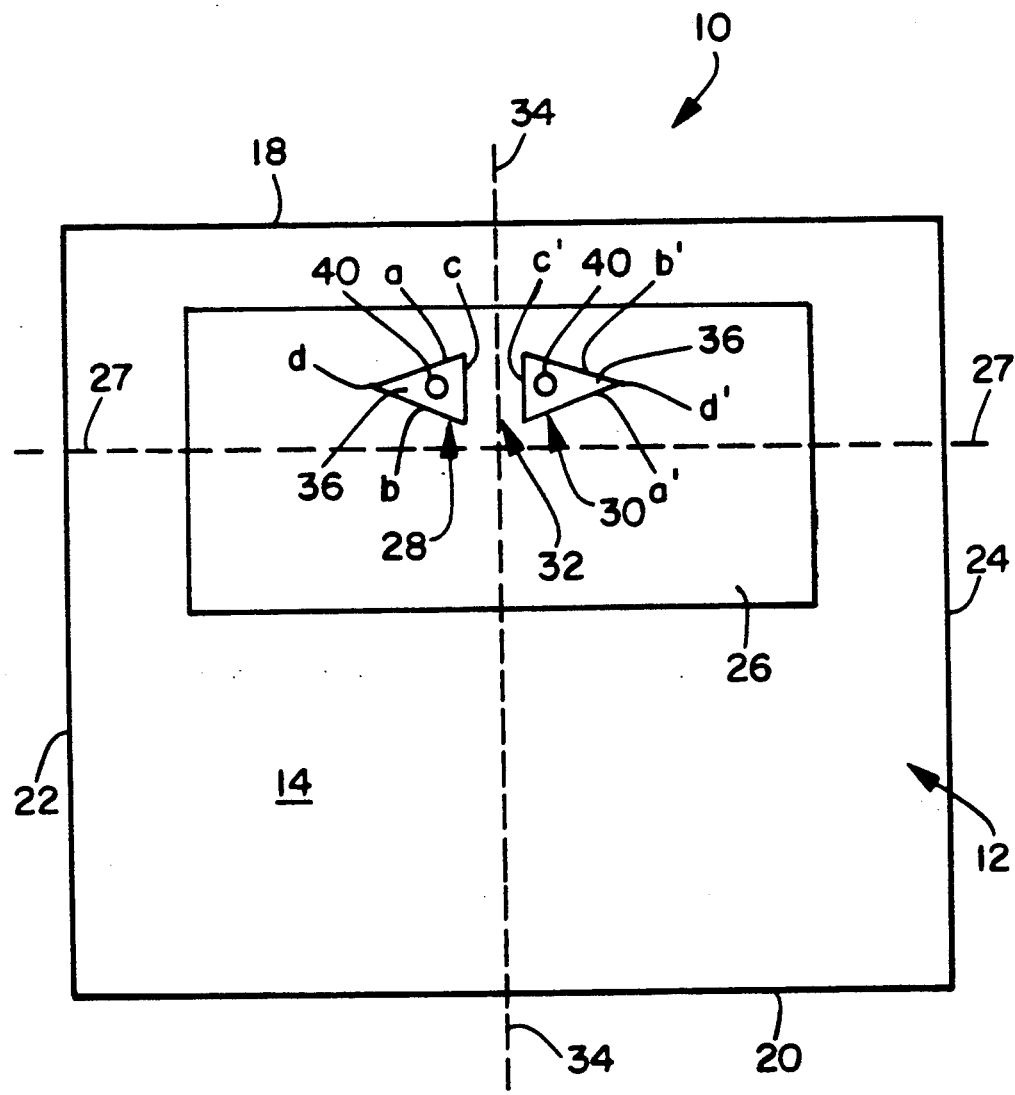
FIG. 1 is a top plan view of a central venous catheter patient cover according to the present invention.

Referring to FIG. 1, there is shown a patient cover or drape 10 according to the present invention. The drape 10 includes a mainsheet 12 having a top surface 14 and a bottom surface 16, a top edge 18 and a bottom edge 20 joined by opposed side edges 22 and 24. The mainsheet 12 is made from any material suitable for use in such situations including both woven and nonwoven materials. One preferred material is a repellent nonwoven material sold as Evolution ® fabric by the Kimberly-Clark Corporation of Neenah, Wisconsin. Due to the nature of the procedure for which the present invention is used, it is desirable that the mainsheet have dimensions of approximately 71 by 76 inches (length by width). This size permits the mainsheet 12 to cover the entire upper body portion including the face of the patient who is being catheterized.

Attached to the top surface 14 of the mainsheet 12 is a reinforcement sheet 26. The reinforcement sheet 26 is made from an absorbent nonwoven material which is capable of absorbing 300 to 500% of its own weight in liquids such as water and irrigation fluids. The material also has a 4-5 rating on the Martindale Abrasion Test. The basis weight of this material should be greater than that of the mainsheet 12. Attachment of the reinforcement sheet 26 to the mainsheet 12 may be by any suitable means such as adhesives, thermal bonding and ultrasonic bonding as well as stitching and tape. It is desirable that the reinforcement sheet 26 have dimensions of approximately 29 by 48 inches (length by width). The reinforcement sheet 26 is positioned such that the transverse centerline 27, from side edge to side edge, of the sheet is closer to the top edge 18 than the bottom edge 20 of the mainsheet 12.

Positioned in and extending completely through the mainsheet 12 and reinforcement sheet 26 are a first fenestration 28 and a second fenestration 30 each of which are triangular in shape, have three sides and three apices. The triangular fenestrations 28 and 30 are positioned relative to one another such that one side of each triangle is parallel with one side of the other triangle (a,a', b,b', c,c'). As a result, a strip 32 with generally parallel sides if formed between the two triangles from the material of the mainsheet 12 and reinforcement sheet 26. The strip 32 should be sufficiently wide to cover the cervical and thoracic vertebra for subclavian insertion and the sternum and rib cage for basilic catheterization. Generally, a strip approximately 2-3 inches in width should be sufficient for this purpose. In the embodiment shown in FIG. 1, one apex of each triangle (d,d') will be closer to the adjacent side edge 22, 24 respectively, of than mainsheet 12 than any of the other apices of the same triangular fenestration and the two triangular fenestrations will be symmetrical about a longitudinal axis 34 of the drape or cover 10.

Figure 2:
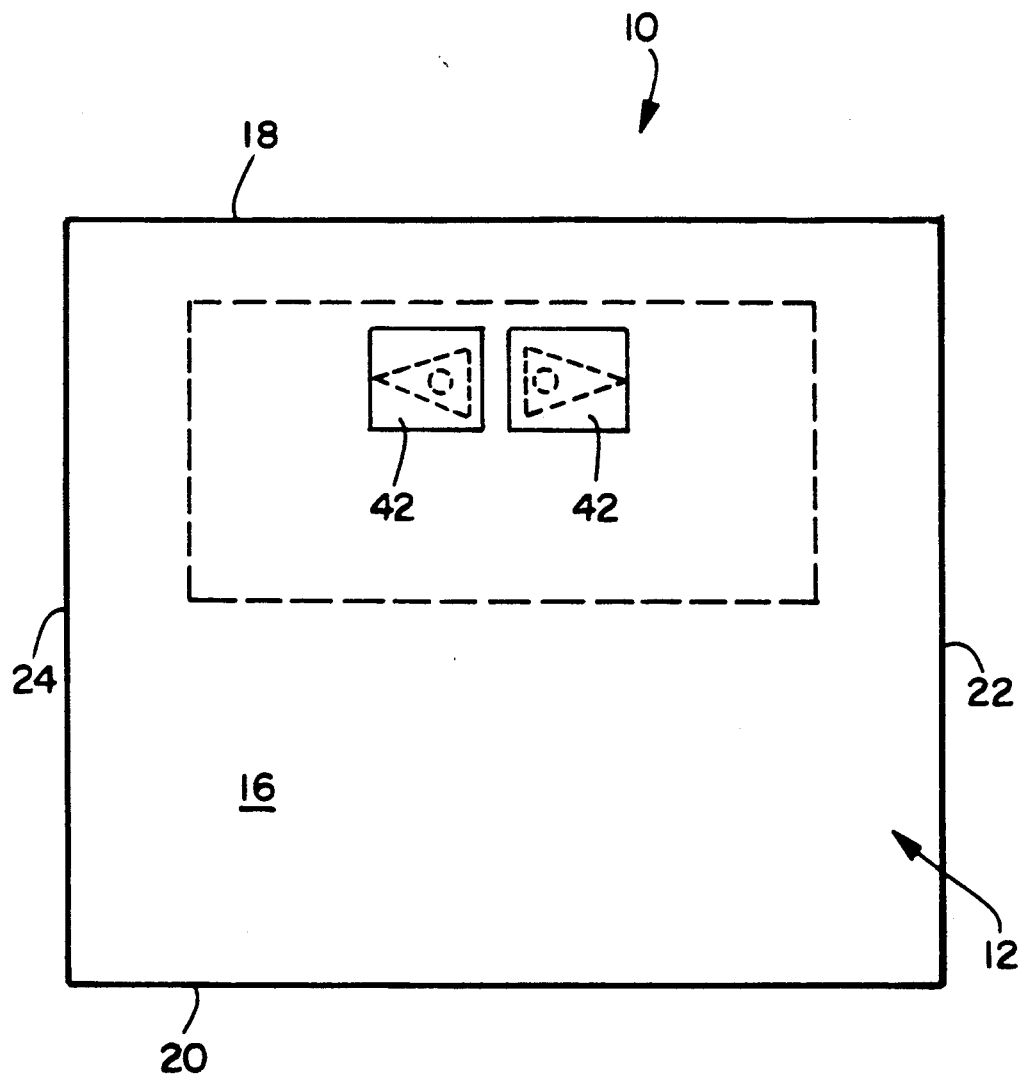
FIG. 2 is a bottom plan view of a central venous catheter patient cover according to the present invention.

Each of the fenestrations 28 and 30 are covered with an adhesive incise material 36 the composition and use of which is well known to one skilled in the art of drape construction. The incise material for each fenestration 28 and 30 has an access port 40 with the exposed adhesive side of each incise material of each fenestration 28 and 30 being covered by a release sheet 42. See FIG. 2. In constructing the drape 10 of the present invention, the incise material 36 may be positioned on top of the reinforcement sheet 26; between the reinforcement sheet 26 and the mainsheet 12; or on the bottom surface 16 of the mainsheet 12. Irrespective of the specific configuration, the release sheet 42 is attached to and removed from the incise 36 from the bottom surface 16 of the mainsheet 12.

In use, the patient gown 10 is unfolded, one or both of the release sheets 42 are removed, and the incise 36 is attached to the patient such that the fenestration 28 and 30 are placed over the subclavian area or antecubital fossa so that the catheter(s) can be inserted into either or both the left and right central vein through the ports 40. Due to the size of the drape 10 and the location of the fenestrations 28 and 30, the head, neck and torso of the patient (not shown) are covered, thereby creating a sterile field which helps lower the risk of infection.

The central venous catheter patient cover of the present invention is designed to offer maximum protection to the patient during the insertion of the catheter. There is adequate material in the mainsheet 12 at the top of the cover 10 to cover the patient's head, shoulders and arms. The remaining portion of the fabric covers the rest of the patient and is designed to reduce patient exposure in an attempt to limit the opportunity for the patient to become infected. Cross-contamination between the patient and the catheter inserter is further reduced by the use of the reinforcement material 26 around the fenestrated areas 28 and 30. One material suitable for the reinforcement sheet 26 is the CONTROL PLUS ® Absorbent Fabric manufactured and sold by Kimberly-Clark Corporation of Neenah, Wisconsin. This reinforcement material will absorb any exudate from the health care worker inserting the catheter. It will also serve to absorb extra fluid or spills that might come in contact with the catheterization site.

The use of incise stabilizes the patient cover on the patient and allows the health care worker to have clear visibility in finding the correct position for inserting the catheter. Presenting the fenestration in triangular shape provides the health care worker with maximum visibility and replicates the conventional technique of preparing the patient with three separate towels and clamping them in place. The opening or port 40 in the incise material 36 is generally about 3 inches in diameter and allows the catheter to be readily inserted without any cutting, puncturing or further modification of the patient cover. The release sheet 42 on the reverse side of the patient cover 10 permits the health care worker to position the cover aseptically and without having to compromise sterile techniques. Although most of the applications for this bilateral patient cover will be subclavian, it can also be used for insertion in the basilic area of the patient.

Having thus described the invention in detail, it should be appreciated that various modifications and changes can be made in the present invention without departing from the spirit and scope of the following claims.

We claim:

1. A central venous catheter patient cover comprising:
   a mainsheet having a top surface and a bottom surface, a top edge and a bottom edge joined by opposed side edges,
   a reinforcement sheet attached to said top surface and being spaced equidistant from said opposed side edges and positioned between said top and bottom edges of said mainsheet such that said reinforcement sheet is closer to said top edge than said bottom edge of said mainsheet,
   said mainsheet and said reinforcement sheet defining a first fenestration and a second fenestration therein, each of said fenestrations extending completely through said mainsheet and said reinforcement sheet, each of said fenestrations being triangular in shape with three apices and sides with one side of each triangle being parallel with one side of the other triangle, said first and second fenestrations forming a strip therebetween from said mainsheet and reinforcement sheet approximately one to six inches in width, said fenestrations being positioned closer to said top edge than to said bottom edge of said mainsheet.

2. The central venous catheter patient cover of claim 1 wherein one apex of each fenestration is closer to an adjacent one of the opposed side edges than any other apices of the same fenestration and said fenestrations are symmetrically positioned about a longitudinal axis of said patient cover.

3. The central venous catheter patient cover of claim 2 wherein each of said fenestrations are covered with an incise material containing a port to expose a portion of a patient's skin for selective insertion of a central venous catheter.

* * * * *